United States Patent
Enomura et al.

(10) Patent No.: US 10,287,232 B2
(45) Date of Patent: May 14, 2019

(54) METHOD FOR PRODUCING AN ORGANIC COMPOUND IN A ROTATING FORCED THIN-FILM MICROREACTOR

(71) Applicant: M. TECHNIQUE CO., LTD., Izumi-shi, Osaka (JP)

(72) Inventors: Masakazu Enomura, Izumi (JP); Daisuke Honda, Izumi (JP); Kazutaka Takeda, Izumi (JP)

(73) Assignee: M. TECHNIQUE CO., LTD., Izumi-Shi, Osaka (JP)

( * ) Notice: Subject to any disclaimer, the term of this patent is extended or adjusted under 35 U.S.C. 154(b) by 0 days.

(21) Appl. No.: 15/739,075

(22) PCT Filed: Jun. 30, 2016

(86) PCT No.: PCT/JP2016/069509
§ 371 (c)(1),
(2) Date: Dec. 21, 2017

(87) PCT Pub. No.: WO2017/002938
PCT Pub. Date: Jan. 5, 2017

(65) Prior Publication Data
US 2018/0186722 A1    Jul. 5, 2018

(30) Foreign Application Priority Data

Jun. 30, 2015 (JP) .................................. 2015-132076

(51) Int. Cl.
| | | |
|---|---|---|
| *C07C 67/343* | (2006.01) | |
| *B01J 31/02* | (2006.01) | |
| *C07C 67/333* | (2006.01) | |
| *C07C 69/757* | (2006.01) | |
| *C07B 61/00* | (2006.01) | |
| *B01J 19/00* | (2006.01) | |
| *B01J 19/20* | (2006.01) | |
| *B01J 19/18* | (2006.01) | |

(52) U.S. Cl.
CPC ......... *C07C 67/343* (2013.01); *B01J 19/0066* (2013.01); *B01J 19/0093* (2013.01); *B01J 19/18* (2013.01); *B01J 19/1887* (2013.01); *B01J 19/20* (2013.01); *B01J 31/02* (2013.01); *B01J 31/0239* (2013.01); *C07B 61/00* (2013.01); *C07C 67/333* (2013.01); *C07C 69/757* (2013.01)

(58) Field of Classification Search
CPC ... C07C 67/343; C07C 67/333; C07C 69/757; C07C 69/12; C07C 9/15; B01J 19/0093; B01J 31/239; B01J 19/20; B01J 19/00; B01J 31/02; B01J 31/0239; B01J 19/0066; B01J 2219/00889; C07B 61/00
See application file for complete search history.

(56) References Cited

U.S. PATENT DOCUMENTS

| | | | | |
|---|---|---|---|---|
| 3,883,616 A | * | 5/1975 | Hozumi | ................ C08F 279/02 525/243 |
| 2004/0082804 A1 | * | 4/2004 | Brophy | ................ B01J 19/0093 560/1 |
| 2006/0286015 A1 | | 12/2006 | Holl | |
| 2007/0167638 A1 | | 7/2007 | Brophy et al. | |
| 2010/0016615 A1 | | 1/2010 | Nakaya et al. | |
| 2011/0178199 A1 | * | 7/2011 | Enomura | .............. B01F 3/0807 522/3 |
| 2012/0312398 A1 | | 12/2012 | Enomura | |
| 2013/0008514 A1 | | 1/2013 | Enomura | |
| 2015/0321154 A1 | | 11/2015 | Enomura | |

FOREIGN PATENT DOCUMENTS

| | | | |
|---|---|---|---|
| EP | 2216312 A1 | 8/2010 | |
| EP | 2540390 A1 | 1/2013 | |
| EP | 2873453 A1 | 5/2015 | |
| JP | 9-75473 A | 3/1997 | |
| JP | 2006-503894 A | 2/2006 | |
| JP | 2006-150182 A | 6/2006 | |
| JP | 2007-503993 A | 3/2007 | |
| JP | 2009-132675 A | 6/2009 | |

(Continued)

OTHER PUBLICATIONS

Oxley et al. (Evaluation of Spinning Disk Reactor Technology for the Manufacture of Pharmaceuticals, Ind. Eng. Chem. Res., 39, 2175-2182, Published 2000). (Year: 2000).*
Jackson et al. (Mixing Small Volumes for Continuous High-Throughput Flow Cytometry: Performance of a Mixing Y and Peristaltic Sample Delivery, Cytometry 47:183-191, published 2002) (Year: 2002).*
International Search Report, issued in PCT/JP2016/069509, PCT/ISA/210, dated Oct. 4, 2016.
Extended European Search Report, dated Jan. 2, 2019, for European Application No. 16818046.1.

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

At least a first fluid and a second fluid are used and are not miscible with each other. At least the first fluid includes one or two items selected from an organic compound, a reactant, and a phase transfer catalyst. From among the fluids other than the first fluid, at least the second fluid includes at least one item from among the items not selected from the three items. The first fluid and second fluid contain all three items. Each of the fluids are merged in a thin-film fluid formed between processing faces that rotate relative to each other. A phase transfer catalyst reaction occurs in the thin-film fluid. Among the first fluid and the second fluid, at least the fluid containing the phase transfer catalyst is prepared so that the phase transfer catalyst is substantially homogeneously mixed before being introduced between the processing faces.

15 Claims, 4 Drawing Sheets

(56) References Cited

FOREIGN PATENT DOCUMENTS

| WO | WO 2008/050760 A1 | 5/2008 |
| WO | WO 2009/054202 A1 | 4/2009 |
| WO | WO 2011/126124 A1 | 10/2011 |

\* cited by examiner

METHOD FOR PRODUCING AN ORGANIC COMPOUND IN A ROTATING FORCED THIN-FILM MICROREACTOR

TECHNICAL FIELD

The present invention relates to a method for producing organic compound.

BACKGROUND ART

Many organic compounds are soluble in an organic solvent but insoluble in water. On the other hand, many inorganic reacting agents such as sodium hydroxide are soluble in water but insoluble in an organic solvent. Therefore, even if an attempt is made to cause a reaction of an organic compound in an organic solvent with an inorganic reacting agent in an aqueous solution, because they are not miscible to each other, the reaction takes place only in the interface of the phases contacted to each other; and thus, the reaction rate thereof is extremely slow. Accordingly, in an organic synthesis reaction, the reaction is sometimes carried out by adding a phase-transfer catalyst into the reaction system comprising an organic solvent solution of an organic compound and an aqueous solution of a reacting agent while stirring the resulting mixture (Patent Document 1).

The reaction taking place in the interface of two liquids not miscible to each other can be enhanced in its efficiency by using a microreactor. This is because the mass transfer in the interface takes place efficiently as a result of drastic increase in the contact area per unit volume in this interface (Patent Document 2 and Patent Document 3).

However, the microreactor described in Patent Document 2 and Patent Document 3 is of a so-called static type; therefore, in reality, as the diameter of the micro flow path becomes narrower, the pressure loss thereof is inversely proportional to the fourth power of the diameter of the flow path, indicating that a large liquid-feeding pressure is needed so that obtaining a pump capable of feeding the fluid is practically difficult; and in addition, in the case of the reaction accompanied with separation, the micro flow path is closed up due to the phenomenon that the product clogs the flow path as well as bubbles formed by the reaction. Further, because it is expected that the reaction is basically dependent on the diffusion rate of the molecules, the micro space is not effective and applicable in every reaction; and thus, practically, the reaction needs to be studied with a trial-and-error approach so as to finally select a proper one. All in all, there are many problems with the microreactor of this type.

The issue of up-scaling has been dealt with by increasing the number of the microreactor itself, namely, by numbering-up; however, in reality, possible multiplication number thereof is limited to several tens; and thus, the use thereof is prone to valuable products. Further, the increase in the number of equipment means an increase in absolute number of causes of the troubles; and thus, when a trouble such as clogging actually takes place, it is very difficult to identify the problem such as the spot of the trouble.

In order to solve the problems in production of an organic compound as mentioned above, a microreactor of a forced thin film type is proposed wherein fluids are caused to react in a thin film fluid formed between processing surfaces which are disposed in a position they are faced with each other so as to be able to approach to and separate from each other, at least one of which rotates relative to the other (Patent Document 4).

The invention disclosed in Patent Document 4 relates to a production method of an organic compound in which many examples of organic reactions are described; however, there is no disclosure with regard to a phase-transfer catalysis reaction. Nevertheless, as disclosed in Patent Document 4, uniformity of temperature and uniformity of the reaction in the thin film fluid are also high in the microreactor of a forced thin film type; and thus, if the phase-transfer catalysis reaction is applied to it, it is natural to expect a high reaction yield.

Therefore, inventors of the present application tried to carry out the phase-transfer catalysis reaction by using the microreactor of a forced thin film type disclosed in Patent Document 4; but contrary to the expectation, it was found that a favorable result could not be obtained as the yield thereof was about 50%.

PRIOR ART DOCUMENTS

Patent Document

Patent Document 1: Japanese Patent Laid-Open Publication H9-75473
Patent Document 2: Japanese Patent Laid-Open Publication 2006-150182
Patent Document 3: International Patent Laid-Open Publication No. 2008/050760
Patent Document 4: Japanese Patent Laid Open Publication 2009-132675

DISCLOSURE OF THE INVENTION

Problems to be Solved by the Invention

As mentioned above, when an organic compound is produced by the phase-transfer catalysis reaction, there are problems in production of an organic compound using the microreactor of a static type. On the other hand, the reaction yield is low when the microreactor of a forced thin film type is used. The present invention solves the problems associated with the use of the microreactor mentioned above in production of an organic compound with the phase-transfer catalysis reaction.

Means for Solving the Problems

Namely, the present invention provides a method for producing an organic compound wherein the method uses at least two fluids, a first fluid and a second fluid, which are not miscible to each other; of the fluids, at least the first fluid contains one or more entities selected from three entities composed of an organic compound, a reacting agent, and a phase-transfer catalyst; of the fluids other than the first fluid, at least the second fluid contains at least one entity not selected from the three entities; and a fluid containing all the three entities in entirety of the first fluid and the second fluid is processed.

Combinations of the fluids to satisfy the above conditions are as follows.
The Combination 1-1
The first fluid: an organic compound and a reaction agent
The second fluid: an organic compound, a reaction agent and a phase-transfer catalyst
The Combination 1-2
The first fluid: an organic compound and a reaction agent
The second fluid: an organic compound and a phase-transfer catalyst The Combination 1-3
The first fluid: an organic compound and a reaction agent
The second fluid: a reaction agent and a phase-transfer catalyst
The Combination 1-4
The first fluid: an organic compound and a reaction agent
The second fluid: a phase-transfer catalyst only
The Combination 1-5
The first fluid: an organic compound and a reaction agent
The second fluid: a phase-transfer catalyst and other fluids
The Combination 2-1
The first fluid: an organic compound and a phase-transfer catalyst
The second fluid: an organic compound, a reaction agent and a phase-transfer catalyst
The Combination 2-2
The first fluid: an organic compound and a phase-transfer catalyst
The second fluid: a reaction agent and a phase-transfer catalyst
The Combination 2-3
The first fluid: an organic compound and a phase-transfer catalyst
The second fluid: a reaction agent and an organic compound
The Combination 2-4
The first fluid: an organic compound and a phase-transfer catalyst
The second fluid: a reaction agent only
The Combination 2-5
The first fluid: an organic compound and a phase-transfer catalyst
The second fluid: a reaction agent and other fluids
The Combination 3-1
The first fluid: a reaction agent and a phase-transfer catalyst
The second fluid: an organic compound, a reaction agent and a phase-transfer catalyst
The Combination 3-2
The first fluid: a reaction agent and a phase-transfer catalyst
The second fluid: an organic compound and a phase-transfer catalyst
The Combination 3-3
The first fluid: a reaction agent and a phase-transfer catalyst
The second fluid: a reaction agent and an organic compound
The Combination 3-4
The first fluid: a reaction agent and a phase-transfer catalyst
The second fluid: an organic compound only
The Combination 3-5
The first fluid: a reaction agent and a phase-transfer catalyst
The second fluid: an organic compound and other fluids
The Combination 4-1
The first fluid: an organic compound
The second fluid: an organic compound, a reaction agent and a phase-transfer catalyst
The Combination 4-2
The first fluid: an organic compound
The second fluid: a reaction agent and a phase-transfer catalyst
The Combination 5-1
The first fluid: a reaction agent
The second fluid: an organic compound, a reaction agent and a phase-transfer catalyst
The Combination 5-2
The first fluid: a reaction agent
The second fluid: an organic compound and a phase-transfer catalyst The fluids with the combinations mentioned above are introduced into a thin film fluid formed between processing surfaces which are disposed in a position they are faced with each other so as to be able to approach to and separate from each other, at least one of which rotates relative to the other, whereby converging the first fluid and the second fluid to cause a reaction (phase-transfer catalysis reaction) between an organic compound and a reacting agent in the presence of a phase-transfer catalyst in the thin film fluid.

Meanwhile, other than those described above, the other fluid may be arbitrarily included in the first fluid and the second fluid in the above combinations, or may be introduced as a third fluid. A pretreatment process of the reaction process in the thin film fluid is characterized by that, of the first fluid and the second fluid, before a fluid which contains at least the phase-transfer catalyst is introduced into between the processing surfaces, the phase-transfer catalyst contained in the first fluid and/or the second fluid is prepared so as to be mixed substantially homogeneously in the said fluid.

This mixing may be carried out by using an agitator, wherein an agitator such as, for example, an agitator having a rotating blade, may be used. Upon this mixing, it is preferable that, of the first fluid and the second fluid, an agitation energy per unit volume applied to the fluid which contains at least the phase-transfer catalyst be controlled so as to control the yield of the reaction product formed by the reaction, wherein the agitation energy is preferably 2.0 kW·h/m$^3$ or more, while more preferably 4.0 kW·h/m$^3$ or more.

The processing surface is provided with an opening having a concentric circular form, wherein it is preferable that, of the first fluid and the second fluid, at least one fluid be introduced into between the processing surfaces through this opening.

Among the combinations mentioned above, the following combination is particularly preferable. Namely, any one of the first fluid and the second fluid is made to contain at least the organic compound, and any one of the first fluid and the second fluid other than the above is made to contain at least the reacting agent. Meanwhile, the reacting agent may be contained in both the first fluid and the second fluid. Likewise, the organic compound may be contained in both the first fluid and the second fluid.

In such conditions, the phase-transfer catalyst is contained at least in any one of the first fluid and the second fluid; and the fluid containing the phase-transfer catalyst is subjected to the pretreatment so as to homogeneously mix the phase-transfer catalyst into the fluid containing the organic compound or the reacting agent. Especially, it is more preferable that, of the first fluid and the second fluid, one fluid is an organic phase containing the organic compound, or the organic compound and the reacting agent, and another fluid is an aqueous phase containing the reacting agent. With this, the phase-transfer catalyst is contained at least in any one of the first fluid and the second fluid; and the fluid containing the phase-transfer catalyst is subjected to the pretreatment so as to homogeneously mix the phase-transfer catalyst into the fluid containing the organic compound or the reacting agent.

Advantages

When producing an organic compound by the phase-transfer catalysis reaction, by using the production method of the present invention, the production method of the organic compound with a high reaction yield without problems in production can be provided.

Figure 1:
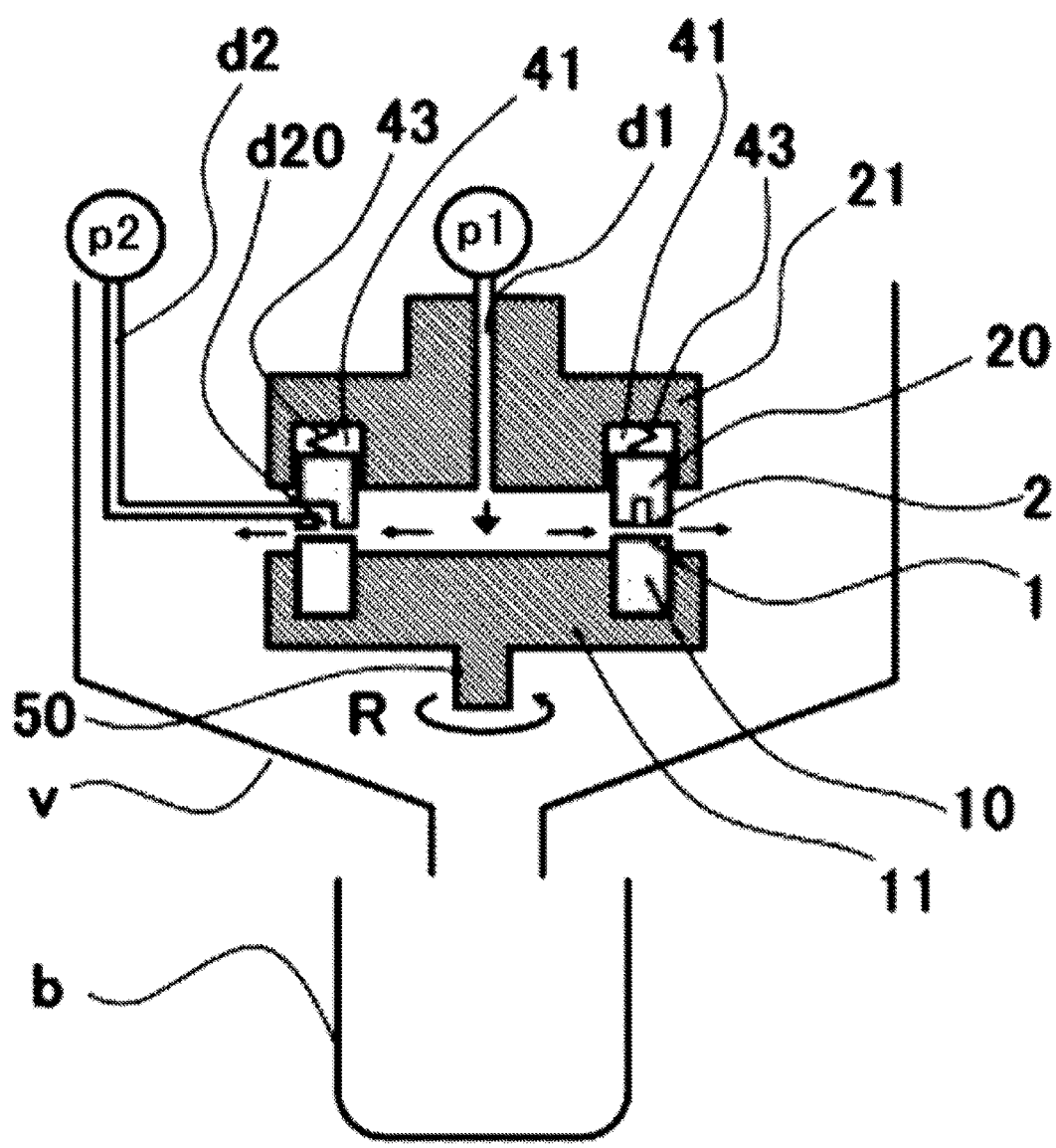
FIG. 1
This illustrates the rough cross section view of the microreactor used in the method for producing the organic compound according to the embodiment of the present invention.

This is the enlarged view of the essential part of a processing surface of the microreacotr shown in FIG. 1.

FIG. 3

This is an explanatory view of the stirrer that is used in the embodiment of production method for an organic compound which relates to an embodiment for the present invention.

FIG. 4

This is an explanatory view of the essential part of the same stirrer.

BEST MODES FOR CARRYING OUT THE INVENTION

Hereinafter, detailed explanation of the present invention will be made; but a technical range of the present invention is not limited by the following Embodiments.

When carrying out the phase-transfer catalysis reaction, the present invention uses a microreactor of a forced thin film type in which the fluids to be used for the reaction are caused to react in a thin film fluid formed between processing surfaces which are disposed in a position they are faced with each other so as to be able to approach to and separate from each other, at least one of which rotates relative to the other.

Combination of the organic compound and/or the reacting agent applied to the present invention is not particularly restricted. The organic compound and/or the reacting agent each may be two or more kinds. Two organic compounds each may be separated into a fluid mainly comprising water and a fluid mainly comprising an organic solvent. Compounds to be used as the organic compound and/or the reacting agent may be, for example, the same as those used in conventional two phase reaction of an aqueous phase and an organic phase.

The reaction suitably used in the present invention may be a reaction in which the organic compound is hydrophobic and the reacting agent is water-soluble.

The hydrophobic organic compound is not particularly restricted, wherein compounds generally having low solubility into water and being soluble in an organic solvent having low polarity may be widely used, so that illustrative example thereof includes hydrocarbon compounds, halogenated hydrocarbon compounds, ketone compounds, and ester compounds. The ketone compound is not particularly restricted, wherein illustrative example thereof includes acetone, methyl ethyl ketone, diethyl ketone, cyclohexanone, acetophenone, and benzophenone.

The water-soluble reacting agent is not particularly restricted, wherein illustrative example thereof includes inorganic acids, inorganic bases, metal salts of organic acids, and inorganic salts.

The inorganic acid is not particularly restricted, wherein illustrative example thereof includes nitric acid, sulfuric acid, hydrochloric acid, and phosphoric acid. The inorganic base is not particularly restricted, wherein illustrative example thereof includes sodium hydroxide, potassium hydroxide, and lithium hydroxide.

The metal salt of an organic acid is not particularly restricted, wherein illustrative example thereof includes sodium p-toluenesulfonate, potassium p-toluenesulfonate, sodium methanesulfonate, potassium methanesulfonate, sodium trifluoromethanesulfonate, potassium trifluoromethanesulfonate, sodium acetate, and potassium acetate.

The inorganic salt is not particularly restricted, wherein illustrative example thereof includes sodium nitrate, potassium nitrate, iron nitrate, copper nitrate, silver nitrate, sodium sulfate, potassium sulfate, copper sulfate, silver sulfate, sodium chloride, potassium chloride, copper chloride, sodium chloride, sodium phosphate, potassium phosphate, sodium carbonate, and potassium carbonate.

The organic solvent immiscible with water to be used in the phase-transfer catalysis reaction is not particularly restricted, wherein illustrative example thereof includes hydrocarbon compounds, ester compounds, halogenated hydrocarbon compounds, ether compounds, and mixtures of these compounds.

The hydrocarbon compound is not particularly restricted, wherein illustrative example thereof includes pentane, hexane, heptane, octane, nonane, decane, cyclopentane, cyclohexane, benzene, toluene, and xylene.

The ester compound is not particularly restricted, wherein illustrative example thereof includes ethyl acetate, propyl acetate, isopropyl acetate, butyl acetate, methyl propionate, ethyl propionate, ethyl lactate, and butyl lactate.

The halogenated hydrocarbon compound is not particularly restricted, wherein illustrative example thereof includes dichloromethane, 1,2-dichloroethane, chloroform, carbon tetrachloride, 1,1,2,2-tetrachloroethane, chlorobenzene, and 1-chloronaphthalene.

The ether compound is not particularly restricted, wherein illustrative example thereof includes diethyl ether, diisopropyl ether, methyl tert-butyl ether, and cyclopentyl methyl ether.

The phase-transfer catalyst in the present invention is the catalyst to be used for the reaction between a water-insoluble organic compound and a reacting agent which is water-soluble but insoluble in an organic solvent. Illustrative example of the catalyst includes quaternary ammonium salts, phosphonium salts, crown ethers, and polyethylene glycol. Illustrative example of the quaternary ammonium salt includes tetraethyl ammonium fluoride, tetrabutyl ammonium fluoride, tetramethyl ammonium fluoride, acetylcholine chloride, benzyl dimethyl tetradecyl ammonium chloride hydrate, (3-acrylamidepropyl) trimethyl ammonium chloride, benzethonium chloride, benzoylcholine chloride, benzoylacetyl cetyl dimethyl ammonium chloride, benzalkonium chloride, benzyl dimethyl phenyl ammonium chloride, benzyl triethyl ammonium chloride, benzyl trimethyl ammonium chloride, trimethyl acetohydrazide ammonium chloride, benzyl dimethyl stearyl ammonium chloride, benzyl tributyl ammonium chloride, N-benzyl cinchonidium chloride, N-benzyl quinidinium chloride, N-benzyl quininium chloride, N-benzyl cinchoninium chloride, benzyl dodecyl dimethyl ammonium chloride, 1-butyl-1-methyl pyrrolidinium chloride, bis(2-hydroxyethyl)dimethyl ammonium chloride, bethanechol chloride, carnitine chloride, chlorocholine chloride, choline chloride, carbamyl choline chloride, (3-chloro-2-hydroxypropyl) trimethyl ammonium chloride, carnitine chloride, lauroylcholine chloride, dodecyl trimethyl ammonium chloride, decyl trimethyl ammonium chloride, dimethyl distearyl ammonium chloride, diallyl dimethyl ammonium chloride, didodecyl dimethyl ammonium chloride, hexadecyl trimethyl ammonium chloride, hexamethonium chloride tetrabutyl ammonium chloride, dodecyl trimethyl ammonium chloride, methacholine chloride (2-methoxyethoxymethyl) triethyl ammonium chloride, triethyl methyl ammonium chloride, methacroylcholine chloride, β-methylcholine chloride, n-octyl trimethyl ammonium chloride, triethyl phenyl ammonium chloride, trimethyl phenyl ammonium chloride, trimethyl stearyl ammonium chloride, succinylcholine chloride, stachydrine hydrochloride, tetraethyl ammonium chloride, tetramethyl ammonium chloride, trioctyl methyl ammonium chloride, trimethyl tetradecyl ammonium chloride, trimethyl [2,3-(dioleyloxy)propyl] ammonium chloride, methyl tri-n-octyl ammonium chloride, tetraamyl ammonium chloride, tetrapropyl ammonium chloride, trimethyl [3-(triethoxysilyl)propyl] ammonium chloride, tributyl methyl ammonium chloride, acetylcholine bromide, benzyl dimethyl tetradecyl ammonium bromide hydrate, (3-acrylamidepropyl) trimethyl ammonium bromide benzethonium bromide, benzoylcholine bromide, benzoyl cetyl dimethyl ammonium bromide, benzalkonium bromide, benzyl dimethyl phenyl ammonium bromide, benzyl triethyl ammonium bromide, benzyl trimethyl ammonium bromide, trimethyl acetohydrazide ammonium bromide, benzyl dimethyl stearyl ammonium bromide, benzyl tributyl ammonium bromide, N-benzyl cinchonidium bromide, N-benzyl quinidinium bromide, N-benzyl quininium bromide, N-benzyl cinchoninium bromide, benzyl dodecyl dimethyl ammonium bromide, 1-butyl-1-methyl pyrrolidinium bromide, bis(2-hydroxyethyl) dimethyl ammonium bromide, bethanechol bromide, chlorocholine bromide, choline bromide, carbamyl choline bromide, (3-chloro-2-hydroxypropyl) trimethyl ammonium bromide, lauroylcholine bromide, dodecyl trimethyl ammonium bromide, decyl trimethyl ammonium bromide, dimethyl distearyl ammonium bromide, diallyl dimethyl ammonium bromide, didodecyl dimethyl ammonium bromide, hexadecyl trimethyl ammonium bromide, hexamethonium bromide, tetrabutyl ammonium bromide, dodecyl trimethyl ammoniumbromide, methacholine bromide, (2-methoxyethoxymethyl) triethyl ammonium bromide, triethyl methyl ammonium bromide, methacroylcholine bromide, β-methylcholine bromide, n-octyl trimethyl ammonium bromide, triethyl phenyl ammonium bromide, trimethyl phenyl ammonium bromide, trimethyl stearyl ammonium bromide, succinylcholine bromide, tetraethyl ammonium bromide, tetramethyl ammonium bromide, trioctyl methyl ammonium bromide, trimethyl tetradecyl ammonium bromide, trimethyl [2,3-(dioleyloxy)propyl] ammonium bromide, methyl tri-n-octyl ammonium bromide, tetraamyl ammonium bromide, tetrapropyl ammonium bromide, trimethyl [3-(triethoxysilyl)propyl] ammonium bromide, tributyl methyl ammonium bromide, acetylcholine iodide, acetyl thiocholine iodide, benzoylcholine iodide, benzoyl thiocholine iodide, benzyl triethyl ammonium iodide, benzyl triethyl ammonium iodide, butyryl choline iodide, benzyl triethyl ammonium iodide, butyryl choline iodide, butyryl thiocholine iodide, choline iodide, decamethonium iodide, 1,1-dimethyl-4-phenyl piperadinium iodide, dimethyl dioctadecyl ammonium iodide, ethyl trimethyl ammonium iodide, ethyl tripropyl ammonium iodide, (ferrocenylmethyl) trimethyl ammonium iodide, (2-hydroxyethyl) triethyl ammonium iodide, β-methylcholine iodide, triethyl phenyl ammonium iodide, trimethyl phenyl ammonium iodide, tetrabutyl ammonium iodide, tetraethyl ammonium iodide, tetramethyl ammonium iodide, tetrapropyl ammonium iodide, tetrahexyl ammonium iodide, tetraamyl ammonium iodide, 3-(trifluoromethyl) phenyl trimethyl ammonium iodide, tetra-n-octyl ammonium iodide, tetraheptyl ammonium iodide, tetraheptyl ammonium iodide, trimethyl [2-[trimethylsilyl]methyl]benzyl] ammonium iodide tetramethyl ammonium sulfate, tetraethyl ammonium sulfate, tetrabutyl ammonium sulfate, tetramethyl ammonium nitrate, tetraethyl ammonium nitrate, tetrabutyl ammonium nitrate, tetrabutyl ammonium acetate, tetrabutyl ammonium hydrosulfate, tetrabutyl ammonium trifluorosulfonate, tetramethyl ammonium p-toluenesulfonate, and tetrabutyl ammonium p-toluenesulfonate. Illustrative example of the phosphonium salt includes butyl triphenyl phosphonium chloride, butyl triphenyl phosphonium bromide, pentyl triphenyl phosphonium chloride, pentyl triphenyl phosphonium bromide, allyl triphenyl phosphonium chloride, allyl triphenyl phosphonium bromide, acetonyl triphenyl phosphonium chloride, acetonyl triphenyl phosphonium bromide, benzyl triphenyl phosphonium chloride, benzyl triphenyl phosphonium bromide, tributyl dodecyl phosphonium chloride, tributyl dodecyl phosphonium bromide, methyl triphenyl phosphonium chloride, methyl triphenyl phosphonium bromide, methyl triphenyl phosphonium iodide, ethyl triphenyl phosphonium chloride, ethyl triphenyl phosphonium bromide, ethyl triphenyl phosphonium iodide, tributyl hexadecyl phosphonium bromide, tetraphenyl phosphonium chloride, tetraphenyl phosphonium bromide, tetraphenyl phosphonium iodide, tetraphenyl phosphonium tetraphenylborate, tetraethyl phosphonium chloride, tetraethyl phosphonium bromide, tetraethyl phosphonium tetrafluoroborate, tetraethyl phosphonium hexafluorophosphate, tetrabutyl phosphonium chloride, tetrabutyl phosphonium bromide, tetrabutyl phosphonium tetrafluoroborate, tetrabutyl phosphonium hexafluorophosphate, tetrabutyl phosphonium tetraphenylborate, and tetrabutyl phosphonium hydroxide. Illustrative example the crown ether includes 12-crown 4-ether, 15-crown 5-ether, 18-crown 6-ether, and 24-crown 8-ether. The reaction between an organic compound and a reacting agent in the presence of these catalysts is called as the phase-transfer catalysis reaction.

The reaction that the present invention can be used is not particularly restricted, wherein illustrative example thereof includes the substitution reaction, the oxidation reaction, the reducing reaction, the addition reaction to multiple bonds, the hydrolysis reaction, the alkylation reaction, the epoxidation reaction, the cyclopropane-forming reaction, and the hydrogen migration hydrogenation method.

In the present invention, as the pretreatment of the reaction process in the thin film fluid, of the first fluid and the second fluid, before a fluid which contains at least the phase-transfer catalyst is introduced into between the processing surfaces, the phase-transfer catalyst contained in the first fluid and/or the second fluid is prepared so as to be substantially homogeneously mixed in the said fluid.

In this process, it is preferable to prepare the fluid containing the phase-transfer catalyst by using an agitator having a rotating blade (hereunder, this is sometimes referred to as an agitation blade). Inventors of the present invention prepared the fluid which contains at least the phase-transfer catalyst with changing various conditions of the agitator while repeating trial and error, and then carried out the experiments wherein the fluid thus prepared was introduced into between at least two processing surfaces which are disposed in a position they are faced with each other so as to be able to approach to and separate from each other, at least one of which rotates relative to the other, whereby these fluids were mixed in a thin film formed between the at least two processing surfaces so as to cause the phase-transfer catalysis reaction in the thin film fluid. As a result, it was surprisingly found that there was a relationship between increase or decrease of the agitation energy and the yield of the reaction product formed by this reaction (the relationship that when the former increases, the latter increases, and when the former decreases, the latter decreases).

With this, it became possible to change the yield of the reaction product only by changing the pretreatment condition with fixing the reaction condition; and moreover, by changing both the reaction condition and the pretreatment condition, the yield of the reaction product could be changed more dynamically. In the pretreatment, of the first fluid and the second fluid, the agitation energy per unit volume applied to the fluid containing at least the phase-transfer catalyst is preferably 2.0 kW·h/m$^3$ or more, while more preferably 4.0 kW·h/m$^3$ or more.

Hereunder, the agitation energy will be explained in more detail. Firstly, power P (workload per unit time) of the agitator can be obtained by the following equation (1).

$$\text{Agitation Power } P \text{ [kw]} = N_p \times \rho \times n^3 \times d^5 \qquad \text{Equation (1)}$$

Here, $N_p$: power coefficient (dimensionless number calculated from experiment data. For example, in the case of Clearmix mentioned later (manufactured by M Technique Co., Ltd.), $N_p$=0.95 to 1.05), ρ: density [kg/m$^3$], n: rotation number [rps], and d: rotor's diameter [m].

Next, because the agitation energy (namely, energy applied for agitation) can be expressed by the product of the agitation power and the agitation time (agitation power P [kw]×agitation time t [s]), the agitation energy can be expressed by the following equation.

$$\text{Agitation Energy} = N_p \times \rho \times n^3 \times d^5 \times t \qquad \text{Equation (2)}$$

Further, because the peripheral velocity v has the relationship of v=π×d×n, the equation (2) can be replaced as follows.

$$\text{Agitation Energy} = N_p \times (1/\pi^3) \times \rho \times v^3 \times d^2 \times t \qquad \text{Equation (3)}$$

Here, when the processing amount of the fluid and the container size of the fluid are unified and the identical agitator is used, this can be regarded as the same system, so that the rotor's diameter d [m] becomes constant; and thus, $N_p \times (1/\pi^3) \times d^2$ can be treated as the constant number.

Meanwhile, in this specification the peripheral velocity of the agitation blade means the moving velocity of the agitation blade at the maximum outer diameter portion thereof, wherein specifically this velocity is calculated from the following equation.

$$\text{Peripheral Velocity } v \text{ [m/s]} = r\omega = 2 \times \pi \times r \text{ [m]} \times f \text{ [rpm]}/60$$

Here, r designates the maximum radius of the agitation blade, ω designates the angular velocity, f designates the rotation number of the agitation blade per unit time, and π designates the circumference ratio.

Mixing by agitation for a long period of time using a general stirring chip is not preferable because there are problems including partial decomposition of molecules and ions contained in the fluid; however, agitation time using the agitator having the rotating agitation blade is not limited in the present invention.

(Agitator Having Agitation Blade)

The agitator in the present invention is not particularly restricted so far as it is the agitator having an agitation blade. In the general agitator having a rotating agitation blade, it is said to be a high speed rotation when the peripheral velocity at the front edge of the agitation blade is 1 m/second or higher. The method of agitation is not particularly restricted, wherein illustrative example of the machine to be used for it includes agitation machines and dissolution machines with various shearing methods, friction methods, high pressure jet methods, and ultrasonic wave methods; an emulsifying machine, a dispersing machine, and a homogenizer. Illustrative example of them includes continuous emulsifying machines such as Ultra Turrax (manufactured by IKA Corp.), TK Homomixer (manufactured by PRIMIX Corp.), and TK Homomic Line Flow and Filmix (both are manufactured by PRIMIX Corp.); and batch or both batch and continuous emulsifying machines such as Clearmix (manufactured by M. Technique Co., Ltd.) and Clearmix Dissolver (manufactured by M. Technique Co., Ltd.). Alternatively, the fluid may be prepared by using an ultrasonic homogenizer, an ultrasonic cleaning machine, a high pressure homogenizer, and the like.

Next, with regard to the agitator having the agitation blade, various forms can be used, as mentioned before. One example thereof is the agitator that is provided with an agitation compartment having a screen formed with plural ejection ports and an agitation blade rotating in this compartment, wherein the front edge of the agitation blade is configured so as to rotate with keeping a minute space with an inner surface of the screen. The screen and the agitation blade that rotate relative to each other may be used; and thus, the screen may rotate in the reverse direction to the rotation direction of the agitation blade or may be fixed so as not to rotate. The agitator having this form will be explained in more detail with referring to FIG. 3 and FIG. 4.

This agitator having the agitation blade is inserted through a cap 102 into an accommodation vessel 101 which accommodates a fluid. Hereunder, the agitation blade is referred to as a blade 107 in FIG. 3 and FIG. 4.

Figure 4:
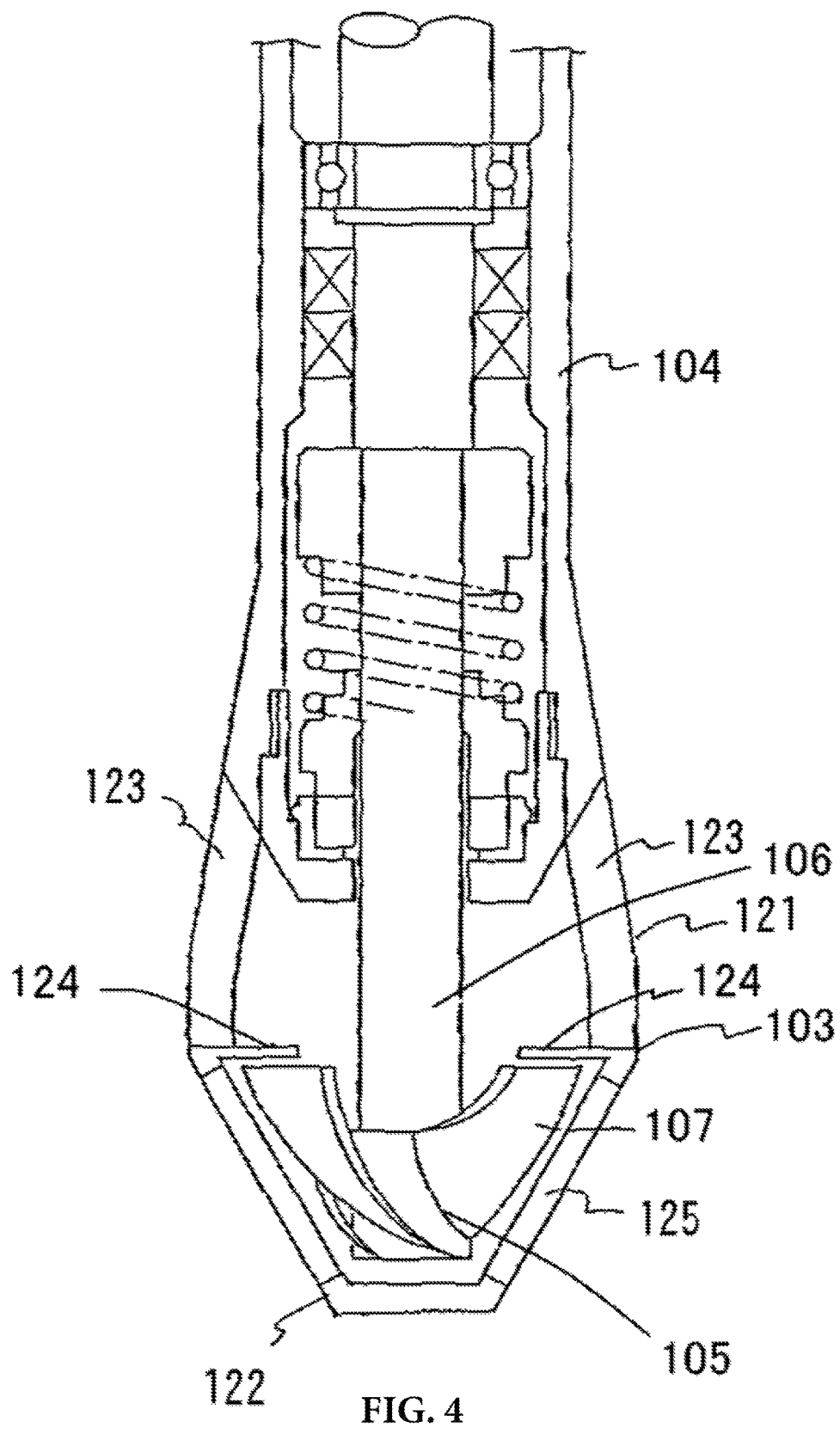

As illustrated in FIG. 4, the agitator having the agitation blade is provided with an agitation compartment 103 and a supporting cylinder 104 which supports the agitation compartment 103. Inside the agitation compartment 103, an impeller 105 is accommodated. The impeller 105 is arranged in the front edge of a rotation axis 106, and the rotation axis 106 is disposed inside the supporting cylinder 104. The rotation axis 106 and the impeller 105 rotate in the direction opposite to the supporting cylinder 104 and the agitation compartment 103. Each of base edges of the supporting cylinder 104 and the rotation axis 106 is connected to separate driving means of rotation (not shown in the figures). The agitation compartment 103 is provided with a housing 121 arranged in the front edge of the supporting cylinder 104 and a screen 122 arranged in the front edge side of the housing 121. A suction port 123 is formed in the housing 121, and an ejection port 125 is formed in the screen 122. With rotation of the impeller 105, a fluid is introduced into the agitation compartment 103 through the suction port 123, and after the fluid is processed for dispersion, dissolution, and the like, it is discharged outside through the ejection port 125. Alternatively, the embodiment in which the ejection port 125 acts as a suction port and the suction port 123 acts as an ejection port may also be employed. In order to partition between inside of the screen 122 and inside of the housing 121, a partition 124 may be arranged or not be arranged.

Especially, the front edge of the blade 107 of the impeller 105 is arranged along the inner wall of the screen 122 with keeping a minute distance. It is preferable that this minute distance be set in the range of about 0.2 to 2 mm. In this minute space a large shear force is given to the fluid, and also a kinetic energy is given to a fluid by rotation of the impeller 105 so that the fluid pressure is increased in a front side of the rotation direction of the blade 107; and thus, the fluid highly pressurized is further accelerated in its speed while passing through the ejection port 125 so as to be ejected outside the screen 122 with forming an intermittent jet stream. On the other hand, in a rear side of the rotation direction of the blade 107, a negative pressure is generated, so that the fluid is sucked into inside the screen 122 from the ejection port 125 immediately after the blade 107 passes the ejection port 125. With these flows of opposite directions, a shear force is generated between the fluids.

The above-mentioned effect can be obtained by relatively rotating the impeller 105 and the agitation compartment 103 having the screen 122. Specifically, the effect can be obtained by rotating the agitation blade, the blade 107, inside the agitation compartment 103 which is in a static state. Alternatively, as in the example mentioned before, the embodiment may be employed in which the ejection port 125 rotates in the opposite direction to the rotation direction of the impeller 105 by rotating the agitation compartment 103 and the impeller 105 in the opposite directions to each other. By so doing, the relative rotation number of these two can be increased so that the shear processing capacity of the fluid can be enhanced further.

The present invention is not limited to this; the screen 122 having the ejection port 125 may be removed while only the housing 121 having the suction port 123 is arranged so as to be rotated. Removal of the screen 122 makes possible not to give a shear force to the fluid, so that the fluid can be dissolved in a short period of time under control of the cavitation. However, it is preferable to arrange the screen 122 in the front edge side of the housing 121, because the intermittent jet flow is generated. Relative rotation of the impeller 105 and the screen 122 applies the shear force to the fluid in the minute space between the inner wall of the screen 122 having the ejection port 125 and the front edge portion of the blade 107, and at the same time, ejects the fluid as the intermittent jet stream from inside to outside of the careen 122 through the ejection port 125. When preparing the fluid containing at least the phase-transfer catalyst, the intermittent jet stream acts effectively for mixing, dissolution, or molecular dispersion of a solvent to the fluid containing at least the phase-transfer catalyst, so that the fluid containing at least the phase-transfer catalyst becomes in the state of mixing or dissolution in a molecular level, or the state of molecular dispersion. It can be presumed that as a result, the phase-transfer catalyst could be mixed extremely homogeneously in the fluid containing an organic compound and/or in the fluid containing a reacting agent thereby contributing to the increase in the yield because the phase-transfer catalysis reaction could take place more uniformly between the processing surfaces of the microreactor of a forced thin film type to be mentioned later.

In the way as described above, because any one or both of the suction port 123 and the ejection port 125 arranged in the agitation compartment 103 rotates, any one or both of the suction position and the ejection position relative to the fluid outside the agitation compartment 103 changes in order; and thus, alienation of the fluid from the circulation can be avoided. Alternatively, the embodiment may be employed in which without arranging the agitation compartment 103, only the impeller 105 is rotated as it is naked.

In order to secure the circulation of the fluid in entire of the accommodation vessel 101, an introduction fin 131 helicoidally wound around the supporting cylinder 104 may be arranged along the longitudinal direction thereof. By rotation of the introduction fin 131 with the supporting cylinder 104, the fluid in the upper portion of the accommodation vessel 101 moves downward along the periphery of the supporting cylinder 104 so as to be introduced into the suction port 123. Alternatively, a circulation fin 132 wound in the direction opposite to the direction of the introduction fin 131 may be arranged. The circulation fin 132 is arranged outside the introduction fin 131 so as to circulate the fluid ejected from the ejection port 125 upward in the accommodation vessel 101.

Figure 3:
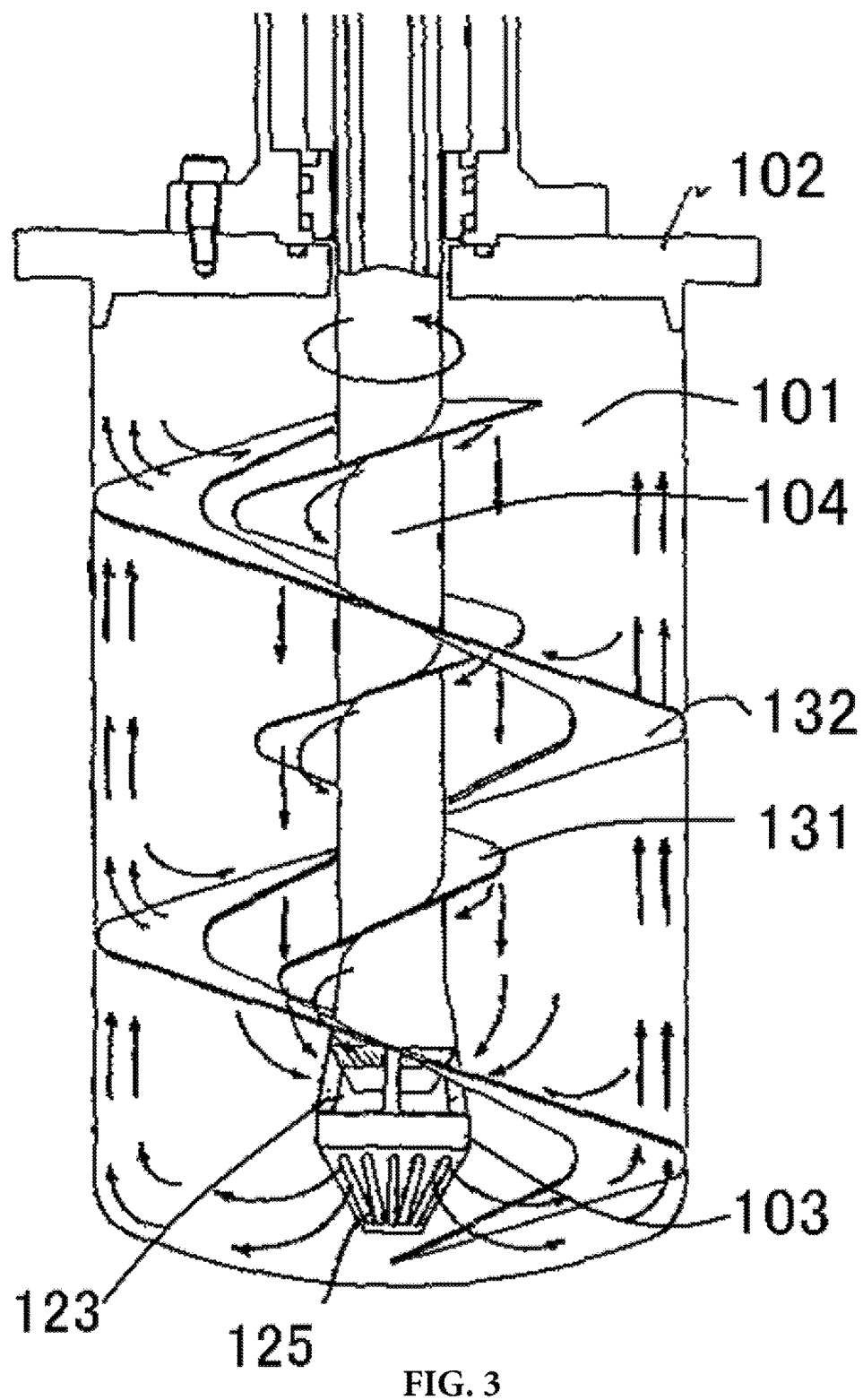

Meanwhile, the agitator illustrated in FIG. 3 and FIG. 4 is commercially available as the product name of Clearmix (manufactured by M Technique Co., Ltd.) mentioned before. Alternatively, Clearmix Dissolver (manufactured by M Technique Co., Ltd.), the machine which is designed by removing the screen from Clearmix (manufactured by M Technique Co., Ltd.), may also be used.

The blade 107 of the impeller 105 in the cross section view (cross section view perpendicular to the axis direction of the rotation axis 106) may be extended in a straight line to a radial direction from center of the impeller 105 with a constant width or with gradual increase in the width as going outside, or extended toward outside with curving. In the axis direction of the rotation axis 106, the blade 107 may be extended in a straight line along the plane including the rotation axis of the rotation axis 106, or may be extended upward and downward with spirally curving or the like.

The maximum outer diameter of the blade 107 of the impeller 105 can be determined arbitrarily in accordance with the embodiment. The ejection port 125 extended in a straight line to the axial direction of the rotation axis 106 (upward and downward directions in the example illustrated in the figure) has been mentioned, but it may be extended with spirally curving or the like. The shape of the ejection port 125 is not necessarily a narrow strip space; and thus, it may be polygonal, circular, elliptical, and so forth. A plurality of ejection port 125 is formed with the same interval in the circumferential direction; but they may be formed with different intervals, while arrangement of a plurality of the ejection port 125 having plural shapes and sizes is not excluded.

(The Microreactor with the Type of a Forced Thin Film)

Hereunder, the case of alkylation reaction will be explained in which the fluids are mixed and contacted with each other by using the microreactor of a forced thin film type.

Figure 2:
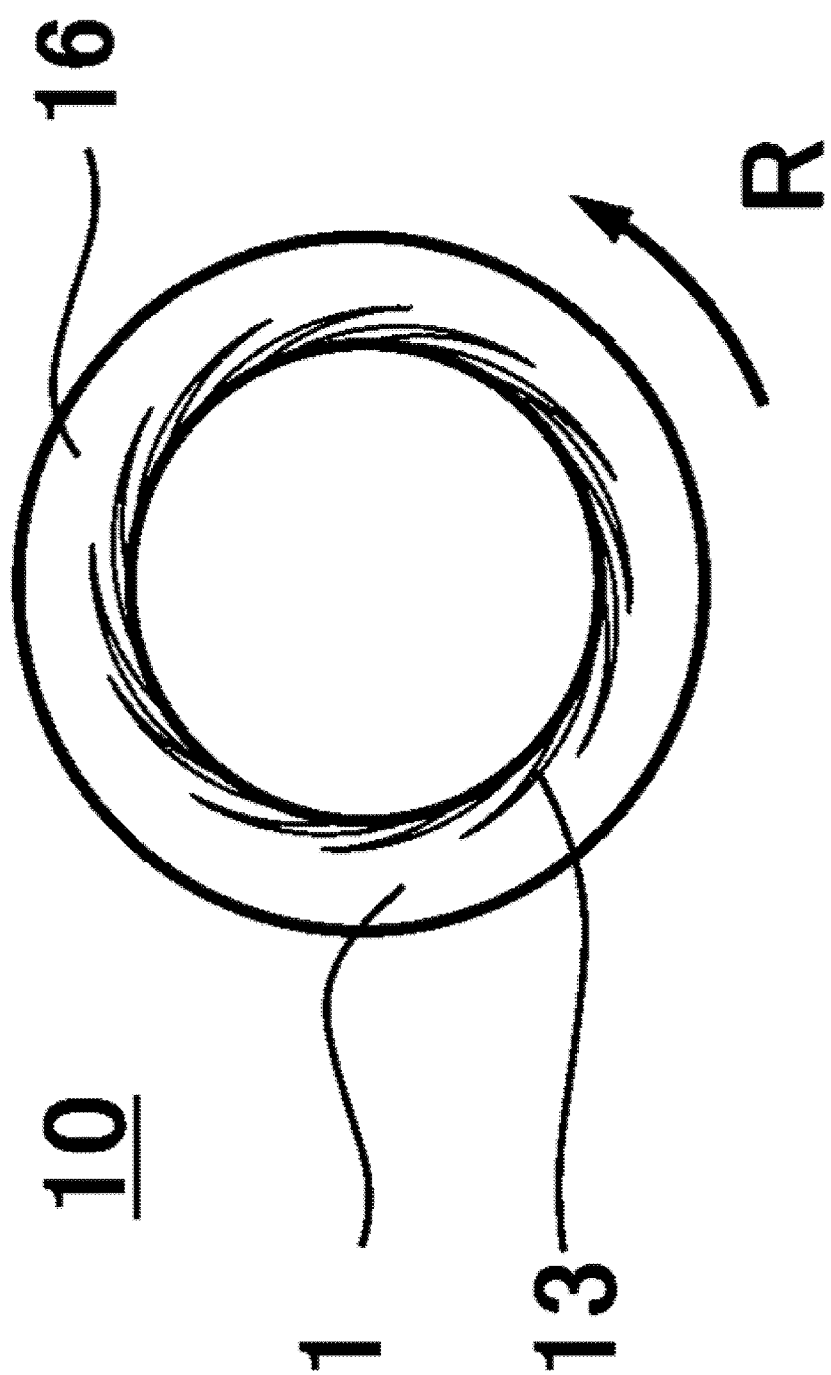
FIG. 2

Meanwhile, as the microreactor, the one shown in FIG. 1, which is the same as the apparatuses described in Patent Document 4, can be used. Hereunder, the microreactor will be described in detail. In FIG. 1 and FIG. 2, the reference character R indicates a rotational direction.

The microreactor (hereafter, also described as the apparatus) of the present embodiment is provided with two processing members of a first processing member 10 and a second processing member 20 arranged opposite to each other, wherein the first processing member 10 rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

Each of the processing surfaces 1 and 2 is connected to a flow path d1 and a flow path d2 of the fluids to be processed, respectively, thereby constituting part of the flow paths of the fluids to be processed. Distance between these processing surfaces 1 and 2 is controlled so as to form a minute space usually in the range of 1 mm or less, for example, in the range of about 0.1 to 50 μm. With this, the fluids to be processed passing through between the processing surfaces 1 and 2 become a forced thin film fluid forced by the processing surfaces 1 and 2.

Then, this apparatus performs a fluid processing in which the first and second fluids to be processed are made to react with each other so as to form the reaction products between the processing surfaces 1 and 2.

To more specifically explain, this apparatus is provided with a first holder 11 for holding the first processing member 10, a second holder 21 for holding the second processing member 20, a surface-approaching pressure imparting mechanism 43, a rotation drive mechanism (not shown in drawings), a first introduction part d1, a second introduction part d2, a fluid pressure imparting mechanism p1 and a fluid pressure imparting mechanism p2. The fluid pressure imparting mechanisms p1 and p2 can be compressors or other pumps.

In the above-mentioned embodiment, the first processing member 10 and the second processing member 20 are disks with ring forms. Material of the processing members 10 and 20 can be not only metal but also carbon, ceramics, sintered metal, abrasion-resistant steel, sapphire, and other metal subjected to hardening treatment, and rigid material subjected to lining, coating, plating, or the like. In the processing members 10 and 20 of the above-mentioned embodiment, the first and the second surfaces 1 and 2 arranged opposite to each other are mirror-polished, and an arithmetic average roughness thereof is in the range of 0.01 to 1.0 μm.

In the above-mentioned embodiment, the second holder 21 is fixed to the apparatus, wherein the first holder 11 attached to a rotary shaft 50 of the rotation drive mechanism fixed to the same apparatus rotates, and thereby the first processing member 10 attached to this first holder 11 rotates relative to the second processing member 20. As a matter of course, the second processing member 20 may be made to rotate, or the both may be made to rotate.

In the present invention, the rotation can be set to a speed of, for example, in the range of 350 to 5000 rpm.

In the above-mentioned embodiment, the second processing member 20 approaches to and separates from the first processing member 10 in the direction of the rotary shaft 50, wherein a side of the second processing member 20 opposite to the second processing surface 2 is accepted in an accepting part 41 arranged in the second holder 21 so as to be able to rise and set. However, in contrast to the above, the first processing member 10 may approach to and separate from the second processing member 20, or both the processing members 10 and 20 may approach to and separate from each other.

The above-mentioned accepting part 41 is a concave portion for accepting the side of the second processing member 20 opposite to the second processing surface 2, and this concave portion is a groove being formed into a ring. This accepting part 41 accepts the second processing member 20 with sufficient clearance so that the side of the second processing member 20 opposite to the second processing surface 2 may rise and set.

The surface-approaching pressure imparting mechanism is a mechanism to generate a force (hereinafter, surface-approaching pressure) to press the first processing surface 1 of the first processing member 10 and the second processing surface 2 of the second processing member 20 in the direction to make them approach each other. The mechanism generates a thin film fluid having minute thickness in a level of nanometer or micrometer while keeping the distance between the processing surfaces 1 and 2 in a predetermined minute distance by the balance between the surface-approaching pressure and the force due to the fluid pressure to separate the processing surfaces 1 and 2 from each other. In the above-mentioned embodiment, the surface-approaching pressure imparting mechanism supplies the surface-approaching pressure by biasing the second processing member 20 toward the first processing member 10 by a spring 43 arranged in the second holder 21.

In addition, the first fluid to be processed which is pressurized with the fluid pressure imparting mechanism p1 is introduced from the first introduction part d1 into the space inside the processing members 10 and 20.

On the other hand, the second fluid to be processed which is pressurized with the fluid pressure imparting mechanism p2 is introduced from the second introduction part d2 via a path arranged inside the second processing member 20 to the space inside the processing members 10 and 20 through an opening d20 formed in the second processing surface.

At the opening d20, the first fluid to be processed and the second fluid to be processed converge and mix with each other.

At this time, the mixed fluid to be processed becomes a forced thin film fluid by the processing surfaces 1 and 2 that keep the minute space therebetween, whereby the fluid is forced to move out from the circular, processing surfaces 1 and 2. The first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Here, as shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1, or, though not shown in the drawing, may be extended straight radially, or bent at a right angle, or jogged; and the concave portion may be continuous, intermittent, or branched. In addition, this depression 13 may be formed also on the second processing surface 2, or on both the first and second processing surfaces 1 and 2. By forming the depression 13 in the manner as mentioned above, the micro-pump effect can be obtained so that the fluid to be processed may be sucked into between the first and second processing surfaces 1 and 2.

It is preferable that the base edge of the depression 13 reach the inner periphery of the first processing member 10. The front edge of the depression 13 is extended to the direction of the outer periphery of the first processing surface 1; the depth thereof is made gradually shallower (smaller) from the base edge to the front edge. Between the front edge of the depression 13 and the outer periphery of the first processing surface 1 is formed a flat plane 16 not having the depression 13.

The opening d20 described above is arranged preferably in a position opposite to the flat surface of the first processing surface 1. Especially, it is preferable to arrange the opening d20 in the position opposite to the flat surface 16 in the downsteam side of the point where the flow direction of the first fluid to be processed that is introduced by micropump effect is changed to the flow direction of the laminar spiral flow formed between the processing surfaces. By so doing, phase-transfer catalysis reaction can be effected under the condition of a laminar flow.

It is preferable that the second introduction part d2 have a direction. For example, the introduction direction from the opening d20 of the second processing surface 2 may be slanted with a prescribed elevation angle (θ1) against the second processing surface 2. Alternatively, the introduction direction from the opening d20 of the second processing surface 2 may have a direction (θ2) in the plane along the second processing surface 2, wherein the introduction direction of the second fluid may be an outward direction from the center thereof in the component of the radius direction of the processing surface, or a forward direction in the component to the rotation direction of the fluid between the rotating processing surfaces. Further, the direction may also be a synthetic direction of the outward direction and the forward direction. As described above, when the flow of the first fluid to be processed is made a laminar flow in the opening d20 and the second introduction part d2 is made to have the direction, the second fluid to be processed can be introduced into between the processing surfaces 1 and 2 with suppressing generation of turbulence to the flow of the first fluid to be processed.

In addition, the fluid discharged to outside the processing members 10 and 20 is collected via a vessel v into a beaker b as a discharged solution. In the embodiment of the present invention, the discharged solution contains the reaction product, as to be described later.

In example shown in FIG. 1, although kinds of the fluid to be processed and numbers of the flow path are set two respectively, they may be three or more. The opening for introduction arranged in each processing member is not particularly restricted in its form, size, and number; and these may be changed as appropriate. In view of reaction efficiency of the phase-transfer catalysis reaction, as shown in FIG. 1, the form of the opening d20 is preferably a concentric circular form surrounding the opening in the center of the processing surface 2 having the form of a ring-like disc. With this, not only the second fluid can be introduced into the space inside the processing members 10 and 20 uniformly in the radius direction of the processing surfaces but also the reaction area under a laminar flow condition in the thin film fluid increases, so that it can be expected that the efficiency of the phase-transfer catalysis reaction, i.e., the yield, increases further more. The opening with a circular form may be continuous or discontinuous. The opening for introduction may be arranged immediately before between the first and second surfaces 1 and 2, or in a further upstream side thereof. When the form of the opening d20 is an independent hole such as a circular hole, the directions (θ1 and θ2) of the second introduction part d2 are involved; but when the form of the opening d20 is the circular form as mentioned above, of the directions of the second introduction part, θ2 is not involved. However, when a means of controlling the flow of the fluid by forming a projection or the like in the second introduction part d2 is arranged so as to give the θ2 direction, the second introduction part d2 may have the directions (θ1 and θ2) even if the form of the opening d20 is the circular form.

In the present invention, it is good enough only if the processing could be effected between the processing surfaces 1 and 2, and an embodiment may also be employed wherein the second fluid to be processed is introduced from the first introduction part d1 and the first fluid to be processed is introduced from the second introduction part d2. For example, the expression "first" or "second" for each fluid has a meaning for merely discriminating an nth fluid among a plurality of the fluids present; and therefore, a third or more fluids can also exist as described before.

EXAMPLES

Hereinafter, the present invention will be explained more specifically by means of Examples. However, the present invention is not limited to the following Examples. In the following Examples, the A solution is the first fluid to be processed that is introduced from the first introduction part d1 of the apparatus shown in FIG. 1; and the B solution is the second fluid to be processed that is introduced from the second introduction part d2 of the same apparatus. The opening d20 having a concentric circular form surrounding the opening in the center of the processing surface 2 having the form of a ring-like disc was used.

As the specific production method of the organic compound according to the present invention, hereunder the example will be given wherein an alkylation reaction to form ethyl 1-benzyl-2-oxocyclopentanoate ester is carried out by using as the organic compound a halogenated alkyl and an active methylene compound capable of becoming a nucleophilic agent, and an inorganic base as the reacting agent.

Meanwhile, the alkylation reaction is a nucleophilic substitution reaction to the halogenated alkyl with the nucleophilic agent formed from the active methylene compound and the inorganic base. In the case of the alkylation reaction, the fluid containing the organic compound is the fluid in which the halogenated alkyl and the active methylene compound are dissolved in a dichloromethane organic solvent, and the fluid containing the reacting agent is the aqueous solution in which the inorganic base and the phase-transfer catalyst are dissolved in pure water.

In the phase-transfer catalysis reaction, the fluid containing the organic compound (B solution) was prepared by dissolving ethyl 2-oxocyclopentanoate ester (active methylene compound; 0.045 mol) and benzyl bromide (halogenated alkyl; 0.07 mol) in dichloromethane (500 mL). The fluid containing the reacting agent (A solution) was prepared as follows: sodium hydroxide (inorganic base; 0.5 mol) and tetrabutylammonium bromide (phase-transfer catalyst; 0.015 mol) were successively added into pure water (10 L), and then the resulting mixture was agitated at room temperature by using Clearmix (manufactured by M Technique Co., Ltd.) for 15 minutes with the rotation number described in Table 1 to obtain 10 L of the A solution. The fluid containing the organic compound as the A solution and the fluid containing the reacting agent as the B solution were introduced into the microreactor of a forced thin film type; and these fluids were mixed and contacted to each other under the processing condition described in Table 1 to cause the phase-transfer catalysis reaction.

Meanwhile, in this example, tetrabutyl ammonium bromide, i.e., the phase-transfer catalyst was dissolved into the fluid containing the reacting agent, and then this was used for the reaction; however, the phase-transfer catalyst dissolved in the fluid containing the organic compound may be used as well.

In Examples 1 to 7 described below, the A solution was prepared under the condition described in Table 1 by using Clearmix (manufactured by M Technique Co., Ltd.) as the agitator having a rotating blade. Meanwhile, Clearmix is disclosed in Japanese Patent No. 5147091 by the present applicant.

In example 8, by using a stirrer as the agitator, the A solution was prepared by stirring at 500 rpm for 15 minutes. Other conditions were the same as those of Examples 1 to 7.

In Comparative Example, the agitator was not used in preparation of the A solution; the solution which was manually agitated was used after it was visually confirmed that the reacting agent was dissolved. Other conditions were the same as those of Examples 1 to 7.

Yield of the alkylation reaction in the present invention was analyzed by the HPLC (high-speed liquid chromatography) method. The HPLC analysis apparatus manufactured by Shimadzu Corp. was used, and YMC-Pack ODS-A (manufactured by YMC Co., Ltd.) was used as the analysis column. Methanol was used as the mobile phase in the HPLC analysis with the flow rate of 0.5 mL/minute and the analysis temperature of 40° C. In the HPLC analysis, the organic phase after the reaction was diluted by 10 folds with methanol, i.e., the mobile phase, and then, the resulting solution was filtrated by the 0.2-μm filter to obtain the filtrate as the analysis sample; thereafter 10 μL of the sample was injected for the HPLC measurement, and the yield was calculated from the ratio of the peak areas derived from the raw material and the product in the chromatogram.

TABLE 1

| | The preparation condition of liquid A | | | The processing condition of the microreactor with the type of a forced thin film | | | |
|---|---|---|---|---|---|---|---|
| | | Agitation | | | | | |
| | Preparation apparatus | Rotation number [rpm] | Peripheral velocity [m/s] | energy per unit volume [kW·h/m³] | Rotation number of the disk [rpm] | Flow amount of liquid A [mL/min] | Flow amount of liquid B [mL/min] | Yield [%] |
| Example 1 | Cleamix | 10000 | 15.7 | 7.44 | 1700 | 100 | 30 | 97 |
| Example 2 | | | | | 1700 | 200 | 30 | 97 |
| Example 3 | | | | | 1700 | 300 | 30 | 98 |
| Example 4 | | | | | 800 | 100 | 30 | 97 |
| Example 5 | | | | | 3600 | 100 | 30 | 98 |
| Example 6 | Cleamix | 6000 | 9.4 | 4.19 | 1700 | 100 | 30 | 93 |
| Example 7 | Cleamix | 3000 | 4.7 | 2.00 | 1700 | 100 | 30 | 88 |
| Example 8 | Stirrer | 500 | 0.79 | 0.13 | 1700 | 100 | 30 | 76 |
| Comparative Example 1 | — | — | — | — | 1700 | 100 | 30 | 51 |

Meanwhile, the preparation condition of the A solution and the processing condition of the microreactor of a forced thin film type that are not described in Table 1 are as follows: blade's diameter of Clearmix agitator; 30 mm, blade's diameter of the stirrer chip; 30 mm, preparation time; 15 minutes, temperature of the A solution supplied; 25° C., temperature of the B solution supplied; 25° C., instrument for measurement of the yield; HPLC analysis instrument (manufactured by Shimadzu Corp.), mobile phase; methanol, column; YMC-Pack ODS-A (manufactured by YMC Co., Ltd.), flow rate; 0.5 mL/minute, column temperature; 40° C., and sample injection amount; 10° L.

From the above results, in Examples 1 to 7 in which the A solution (fluid mainly comprising water which contains the phase-transfer catalyst) was prepared by using the agitator of a high-speed agitation type, the yields of 88% or more were obtained; and especially in Examples 1 to 5, the yields of 97% or more were obtained regardless of the rotation number of the disc of the microreactor of a forced thin film type or of the flow ratio of the A solution and the B solution.

From the above results, it can be seen that when the phase-transfer catalysis reaction is carried out by using the microreactor of a forced thin film type, it is preferable to prepare the solution containing the phase-transfer catalyst more homogenously. From the results of Examples 1 to 8, it can be seen that when the applied agitation energy is decreased, the yield decreases as well.

REFERENCE NUMERALS

1 First processing surface
2 Second processing surface
10 First processing member
11 First holder
20 Second processing member
21 Second holder
d1 First introduction part
d2 Second introduction part
d20 Opening

The invention claimed is:

1. A method for producing an organic compound, wherein at least two fluids, a first fluid and a second fluid, are used, the first fluid and the second fluid are immiscible with each other,
of the two fluids, at least the first fluid contains one or more entities selected from three entities selected from an organic compound, a reacting agent, and a phase-transfer catalyst,
of the fluids other than the first fluid, at least the second fluid contains at least one entity not selected from the three entities,
the first fluid and the second fluid as the whole contains the three entities,
the method comprising:
a preparation step of mixing the phase-transfer catalyst with the fluid containing at least the phase-transfer catalyst so that the phase-transfer catalyst and the first fluid and/or the second fluid are homogeneous, wherein, in the mixing in the preparation step of the first fluid and second fluid, an agitation energy per unit volume applied to the fluid which contains at least the phase-transfer catalyst is 2.0 kW·h/m³ or more, and
a reaction step after the preparation step of converging the first fluid and the second fluid by introducing into a thin film fluid formed between processing surfaces, thereby conducting a phase-transfer catalysis reaction in the thin film fluid, the processing surfaces being disposed in a position they are faced with each other so as to be able to approach to and separate from each other, at least one of which rotates relative to the other, and a distance between is maintained at a predetermined distance of 1 mm or less by a balance between a force in the direction to make the processing surfaces approach and a force in the direction to make the processing surfaces separate.

2. The method for producing the organic compound according to claim 1, wherein the mixing is carried out by using an agitator.

3. The method for producing the organic compound according to claim 2, wherein the agitator is an agitator having a rotating blade.

4. The method for producing the organic compound according to claim 1, wherein,
the processing surface comprises an opening having a concentric circular form,
of the first fluid and the second fluid, at least one fluid is introduced into between the processing surfaces through the opening.

5. The method for producing the organic compound according to claim 1, wherein,
of the first fluid and the second fluid, one fluid is an organic phase which contains the organic compound, or the organic compound and the reacting agent,
another fluid is a water phase which contains the reacting agent, and
the phase-transfer catalyst is contained in at least any one of the first fluid and the second fluid.

6. The method for producing the organic compound according to claim 2, wherein, of the first fluid and the second fluid, an agitation energy per unit volume applied to the fluid which contains at least the phase-transfer catalyst is 2.0 kW·h/m$^3$ or more.

7. The method for producing the organic compound according to claim 3, wherein, of the first fluid and the second fluid, an agitation energy per unit volume applied to the fluid which contains at least the phase-transfer catalyst is 2.0 kW·h/m$^3$ or more.

8. The method for producing the organic compound according to claim 2, wherein,
the processing surface comprises an opening having a concentric circular form,
of the first fluid and the second fluid, at least one fluid is introduced into between the processing surfaces through the opening.

9. The method for producing the organic compound according to claim 3, wherein,
the processing surface comprises an opening having a concentric circular form,
of the first fluid and the second fluid, at least one fluid is introduced into between the processing surfaces through the opening.

10. The method for producing the organic compound according to claim 2, wherein,
of the first fluid and the second fluid, one fluid is an organic phase which contains the organic compound, or the organic compound and the reacting agent,
another fluid is a water phase which contains the reacting agent, and
the phase-transfer catalyst is contained in at least any one of the first fluid and the second fluid.

11. The method for producing the organic compound according to claim 3, wherein,
of the first fluid and the second fluid, one fluid is an organic phase which contains the organic compound, or the organic compound and the reacting agent,
another fluid is a water phase which contains the reacting agent, and
the phase-transfer catalyst is contained in at least any one of the first fluid and the second fluid.

12. The method for producing the organic compound according to claim 4, wherein,
of the first fluid and the second fluid, one fluid is an organic phase which contains the organic compound, or the organic compound and the reacting agent,
another fluid is a water phase which contains the reacting agent, and
the phase-transfer catalyst is contained in at least any one of the first fluid and the second fluid.

13. The method for producing the organic compound according to claim 3, wherein the agitator comprises
an agitation compartment comprising a screen formed with plural ejection ports, and
said rotating blade rotating in said compartment,
wherein a minute space is formed between the inner wall of the screen and the rotating blade.

14. The method for producing the organic compound according to claim 13, wherein said screen rotates in the reverse direction to the rotation direction of said rotating blade.

15. The method for producing the organic compound according to claim 13, wherein said screen is fixed and does not rotate.

\* \* \* \* \*